United States Patent
Yamashita et al.

(12)
(10) Patent No.: US 6,509,498 B1
(45) Date of Patent: Jan. 21, 2003

(54) PROCESS FOR THE PREPARATION OF SORBIC ACID OR SALTS THEREOF

(75) Inventors: Akira Yamashita, Arai (JP); Mitsuhiro Kouno, Arai (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/555,254

(22) PCT Filed: Sep. 21, 1999

(86) PCT No.: PCT/JP99/05125

§ 371 (c)(1),
(2), (4) Date: May 26, 2000

(87) PCT Pub. No.: WO00/18716

PCT Pub. Date: Apr. 6, 2000

(30) Foreign Application Priority Data

Sep. 29, 1998 (JP) .......................... 10-275658

(51) Int. Cl.⁷ .......................... C07C 51/42; C07C 57/10
(52) U.S. Cl. ...................... 562/601; 562/600
(58) Field of Search .................. 562/601, 600

(56) References Cited

U.S. PATENT DOCUMENTS

| | | | | | |
|---|---|---|---|---|---|
| 3,883,585 | A | * | 5/1975 | Fernholz et al. ............ | 260/526 |
| 3,992,442 | A | * | 11/1976 | Kageyama et al. ......... | 260/526 |
| 4,296,243 | A | * | 10/1981 | Sato | |
| 6,214,241 | B1 | * | 4/2001 | Miura ........................ | 210/753 |

FOREIGN PATENT DOCUMENTS

| | | | |
|---|---|---|---|
| JP | 0080773 | * | 12/1966 |
| JP | 4426646 | | 11/1969 |
| JP | 54163516 | | 12/1979 |
| JP | 0048248 | * | 3/1984 |
| JP | A60188346 | | 9/1985 |
| JP | 60-193943 | * | 10/1985 |
| JP | A62103075 | | 5/1987 |
| JP | A62246539 | | 10/1987 |
| JP | A6145097 | | 5/1994 |

OTHER PUBLICATIONS

Organic Chemistry 2d ed. Morrison and Boyd, (1971) p. 525.*
The Chemical Daily Co., Ltd., 12996, pp. 102–103 (1996).

* cited by examiner

Primary Examiner—Mukund J. Shah
Assistant Examiner—Zachary C. Tucker
(74) Attorney, Agent, or Firm—Birch, Stewart, Kolasch & Birch, LLP

(57) ABSTRACT

The invented process produces sorbic acid or its salt through the decomposition of a polyester obtained from ketene and aldehyde, and includes the step of treating a solution containing-sorbic acid or its salt with a chemically activated carbon, which sorbic acid or its salt is produced by the decomposition of the polyester. The treatment with activated carbon is performed, for example, at pH ranging from 5.8 to 7.5 at temperatures ranging from 30° C. to 80° C. The invented process can efficiently remove colored substances and can easily yield a high quality sorbic acid having a satisfactory hue in a high yield.

5 Claims, No Drawings

PROCESS FOR THE PREPARATION OF SORBIC ACID OR SALTS THEREOF

This application is the national phase under 35 U.S.C. § 371 of PCT International Application No. PCT/JP99/05125 which has an International filing date of Sep. 21, 1999, which designated the United States of America.

TECHNICAL FIELD

The present invention relates to a process for producing sorbic acid or its salt which is useful as, for example, food additives. Specifically, the invention relates to a process for producing sorbic acid or its salt including the step of treating sorbic acid or its salt with activated carbon, which sorbic acid or its salt is produced through the decomposition of a polyester obtained from ketene and crotonaldehyde.

BACKGROUND ART

As processes for the commercial production of sorbic acid or its salt, a process of reacting ketene with crotonaldehyde to yield a polyester and hydrolyzing the polyester in the presence of an acid or an alkali, and a process of decomposing the polyester by heat are known.

A crude sorbic acid obtained by the decomposition of the polyester generally contains various colored substances, tar substances, and other impurities and is subjected to purification operations such as treatment with activated carbon, distillation and recrystallization. Particularly, the crude sorbic acid or its salt is often subjected to treatment with activated carbon to remove colored substances.

For example, Japanese Unexamined Patent Application Publication No. 54-163516 discloses a process for preparing a crystalline sorbic acid. This process includes the steps of preparing a polyester from ketene and crotonaldehyde, decomposing the polyester with hydrochloric acid in the presence of, for example, a urea compound to yield a decomposition reaction mixture, separating the decomposition reaction mixture by filtration, and washing the residue to yield a crude sorbic acid, adding a sodium hydroxide aqueous solution to the crude sorbic acid to yield a sodium sorbate aqueous solution, treating the aqueous solution with activated carbon, neutralizing and cooling the treated solution to crystallize sorbic acid. Japanese Examined Patent Application Publication No. 44-26646 discloses a process for producing a crystalline sorbic acid. The process includes the steps of preparing a polyester from ketene and crotonaldehyde, decomposing the polyester with hydrochloric acid having a concentration of 35% by weight or more at temperatures ranging from room temperature to around the boiling point of the hydrochloric acid used, cooling the reaction mixture, separating a crude sorbic acid by filtration, washing the crude sorbic acid with water, putting the washed crude sorbic acid into water, heating and dissolving the sorbic acid to yield a solution, adding activated carbon to the solution, boiling the mixture, and filtering the mixture while heating, and gradually cooling the resulting filtrate to yield a crystalline sorbic acid.

However, according to the investigations made by the present inventors, the ability for removing colored substances or the like contained in a crude sorbic acid greatly varies with the type of activated carbon for use in the treatment with activated carbon. For example, a steam-activated carbon of coconut shell origin is in wide use in the purification of organic compounds but has a low ability for removing colored substance. To obtain a high quality sorbic acid having a satisfactory hue by the use of this type of activated carbon, for example, a crystallization rate in a crystallization process subsequent to the treatment with activated carbon must be decreased or a combination of several complicated purification operations must be employed after the treatment with activated carbon.

DISCLOSURE OF INVENTION

Accordingly, an object of the invention is to provide a process for producing sorbic acid or its salt, which is capable of efficiently removing colored substances and is capable of easily producing a high quality sorbic acid having a satisfactory hue in a high yield.

The present inventors made intensive investigations to achieve the above object, and found that colored substances and other impurities can be efficiently removed by treating a solution containing sorbic acid or its salt with a specific activated carbon, which sorbic acid or its salt is prepared through the decomposition of the polyester.

Specifically, the invention provides a process for producing sorbic acid or its salt by decomposing a polyester obtained from ketene and aldehyde. The process includes the step of treating a solution containing sorbic acid or its salt with a chemically activated carbon, which sorbic acid or its salt is produced by the decomposition of the polyester.

BEST MODE FOR CARRYING OUT THE INVENTION

According to the invention, a polyester obtained from ketene and crotonaldehyde is decomposed to yield sorbic acid or its salt. The polyester is generally shown by the following formula (1):

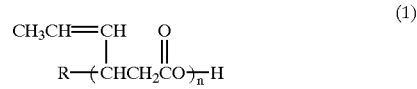

In the above formula, R is an acetoxy group or a hydroxyl group, and n denotes an integer of 2 or more (e.g., about 3 to 40).

The polyester can be obtained by conventional or known processes. For example, the polyester is obtained by reacting ketene with aldehyde in the presence of a catalyst with or without an inert solvent. Such catalysts include, but are not limited to, simple substances or compounds of manganese, cobalt, nickel, zinc, cadmium, and other transition metals; and pyridine, picoline, and other nitrogen-containing basic compounds. Examples of the compounds of the transition metals are oxides; salts of acetic acid, salts of isobutyric acid, salts of isovaleric acid, and salts of other organic acids; salts of sulfuric acid, salts of nitric acid, and salts of other inorganic acids; chlorides and other halides; acetylacetone complex salts, and other complex salts and complexes. Each of these catalysts can be used alone or in combination. The amount of the catalyst differs according to the type of the catalyst, but is generally about 0.1 to 10% by weight relative to the weight of ketene.

The reaction of ketene with crotonaldehyde is performed at temperatures ranging from, for example, about 20° C. to 100° C., and preferably from about 25° C. to 80° C.

A reaction mixture containing a polyester obtained through the reaction of ketene with crotonaldehyde is usually distilled to remove unreacted crotonaldehyde and low boiling impurities, and is then subjected to a decomposition reaction.

The polyester may be decomposed by hydrolysis with an acid or an alkali or by thermal decomposition, but is preferably decomposed by hydrolysis with a mineral acid, particularly with hydrochloric acid, for a higher yield. The polyester is hydrolyzed, for example, at temperatures ranging from about 10° C. to 110° C., and preferably from about 50° C. to 100° C. An extremely low reaction temperature may invite reaction efficiency to decrease, and in contrast, an extremely high reaction temperature may increase the by-production of tar substances and other impurities. When the polyester is hydrolyzed with hydrochloric acid, the concentration of hydrochloric acid is, for example, about 15 to 40% by weight, and preferably about 23 to 36% by weight. An extremely low concentration of hydrochloric acid may invite a decreased reaction rate, and in contrast, an extremely high concentration of hydrochloric acid may invite disadvantages in handling property or ease of operation. The amount of hydrochloric acid in terms of hydrogen chloride is, for example, about 10 to 160 parts by weight, and preferably about 15 to 100 parts by weight, relative to 100 parts by weight of the polyester.

A reaction mixture obtained through the decomposition of the polyester contains colored substances, tar substances, and other impurities by-produced in the reaction, in addition to the sorbic acid or its salt and the catalyst used. The production of a high quality sorbic acid or its salt therefore requires a purification process.

The invention has a main feature of including the step of treating a solution containing the sorbic acid or its salt with a chemically activated carbon, which sorbic acid or its salt is obtained by the decomposition of the polyester.

The treatment with activated carbon can be performed at any point in the purification process of sorbic acid or its salt subsequent to the polyester decomposition process. For example, when the polyester is hydrolyzed in the presence of an acid, the resulting reaction mixture is usually a slurry containing sorbic acid dispersed in water. Generally, the reaction mixture slurry is subjected to solid-liquid separation operation such as filtration or centrifugal separation to yield a crude sorbic acid as a solid, and the crude sorbic acid or its salt (e.g., a potassium salt, a sodium salt, and other alkali metal salts), which is obtained by allowing an alkali metal hydroxide and so on to act upon the sorbic acid, is dissolved in a solvent, and is subjected to the treatment with activated carbon. Water is often used as the solvent for use in the treatment with activated carbon. The water may contain a water-soluble organic solvent such as acetone, methanol, or ethanol.

Chemically activated carbons include a wide variety of activated carbons obtained by impregnating a material with an activating agent and firing (baking) the impregnated material. Such materials for activated carbon include, but are not limited to, wood, sawdust, charcoal, plain ash (carbonized sawdust), fruit shells (coconut shells, walnut shells), fruit seeds, fruit shell coals, fruit seed coals, corn shells, peat, by-products of pulp manufacture, lignin, sugar wastes, molasses, and other materials of plant origin; peat, grass peat, lignite, brown coal, bituminous coal, anthracite, coke, coal tar, coal pitch, petroleum pitch, and other materials of mineral origin; phenol resins, vinylidene chloride resins, acrylic resins, and other synthetic resin-based materials. of these materials, materials of plant origin, especially, sawdust, fruit shells, corn shells, straw of barley, peat, and other woody materials are preferred as they are satisfactorily impregnated with an agent.

The activating agent may be any of agents having dehydration property and oxidizing property with respect to organic compounds. Such agents include, but are not limited to, zinc chloride; phosphoric acid; sulfuric acid; potassium hydroxide, sodium hydroxide, potassium carbonate, sodium carbonate, sodium phosphate, calcium chloride, potassium Aim sulfide, potassium thiocyanate, potassium sulfate, sodium sulfate, and other alkali metal compounds; calcium carbonate, and other alkaline earth metal compounds. As the activating agent, acidic agents such as zinc chloride and phosphoric acid are often used.

The specific surface area of the chemically activated carbon is generally about 200 to 3500 $m^2/g$, preferably about 400 to 2000 $m^2/g$, and more preferably about 1000 to 2000 $m^2/g$. The total pore volume of the chemically activated carbon is generally about 0.1 to 2 ml/g, preferably about 0.2 to 1.6 ml/g, and more preferably about 0.8 to 1.6 ml/g.

The amount of the chemically activated carbon can be appropriately selected within a range not deteriorating the purification efficiency or other properties, and is generally about 1 to 20 parts by weight, and preferably about 2 to 15 parts by weight relative to 100 parts by weight of the sorbic acid or its salt to be treated with activated carbon.

The treating temperature and pH of the solution to be treated in the treatment with activated carbon can be appropriately selected within ranges not deteriorating the purification efficiency and ease of operation. The treating temperature is generally about 20° C. to 100° C., preferably about 30° C. to 80° C., and more preferably about 40° C. to 70° C. The pH of the solution to be treated is generally about 5 to 9, preferably about 5.8 to 7.5, and more preferably about 6.2 to 6.8.

When the sorbic acid or its salt prepared by the decomposition of the polyester is treated with a chemically activated carbon, colored substances can be highly efficiently removed as compared with a treatment with a gas-activated carbon. The detail reason of this has not been clarified, but this is probably because such a chemically activated carbon has a pore size or pore size distribution suitable for the adsorption of colored substances which are by-produced in the polyester decomposition process. Accordingly, the invention can simplify the purification process subsequent to the treatment with activated carbon and can suppress the loss of sorbic acid in the purification process to a low level to thereby efficiently produce a high quality sorbic acid or its salt having a satisfactory hue.

The salts of sorbic acid such as potassium sorbate and sodium sorbate can be prepared by hydrolyzing the polyester with an alkali, or by preparing sorbic acid through, for example, hydrolysis with an acid, and reacting the sorbic acid with, for example, an alkali metal hydroxide to yield a salt in an appropriate step of a subsequent purification process. The invented process can be applied to the salts of sorbic acid, as well as to sorbic acid.

Where necessary, the sorbic acid or its salt treated with activated carbon is subjected to a conventional separation and purification means to further improve the hue and purity. Such separation and purification means include, for example, crystallization, filtration, centrifugal separation, distillation, and recrystallization.

The product sorbic acid and its salts can be used as preservatives for foods such as fish pastes, butters, cheeses, bean pastes, and jams.

The invention treats sorbic acid or its salt with a specific activated carbon, which sorbic acid or its salt is prepared by the decomposition of the polyester, and can efficiently remove colored substances and can easily yield a high quality sorbic acid having a satisfactory hue in a high yield.

The present invention will now be illustrated in further detail with reference to several inventive examples and a comparative example below, which are not intended to limit the scope of the invention. All "parts" are by weight unless otherwise specified.

EXAMPLE 1

To 600 parts of crotonaldehyde, 2 parts of zinc isobutyrate was added as a catalyst, and 170 parts of a ketene gas was introduced at a temperature of 30° C. to 40° C. to perform a reaction. After the completion of reaction, excess crotonaldehyde was removed by distillation under reduced pressure to yield 450 parts of a highly viscous polyester.

To 135 parts of the above-prepared polyester, 110 parts of a concentrated hydrochloric acid having a concentration of 34% by weight was added, and the resulting mixture was heated to 80° C. to decompose the polyester to thereby yield a sorbic acid slurry. The sorbic acid slurry was cooled and was then filtrated under reduced pressure to yield a crude sorbic acid having a moisture content of 20% by weight, a tar content on dry basis of 4% by weight, and a hydrochloric acid content on dry basis of 4000 ppm.

The above-prepared crude sorbic acid (65 g) and a sodium hydroxide aqueous solution were mixed and gradually heated while stirring and adjusting pH of the resulting mixture to 6.5. As a result, a homogenous solution was obtained at a temperature of 55° C. To this solution, 3 g of a zinc chloride-activated carbon [trade name: CARBORAFFIN M, material: wood flour, total pore volume: 1.4 ml/g, specific surface area: 1500 $m^2$/g, a product of Takeda Chemical Industries, Ltd.] was added, and the resulting mixture was stirred for 1 hour. The mixture was then filtrated to remove the activated carbon, and the filtrate was acidified to precipitate sorbic acid, and the precipitated sorbic acid was filtrated and dried. In 8.8 ml of a 1 N-NaOH aqueous solution, 1 g of the above-prepared sorbic acid was dissolved to yield a solution, and the light transmittance of the solution at a wavelength of 400 nm was determined with a spectrophotometer. The solution was found to have a light transmittance of 79.0%.

EXAMPLE 2

A crude sorbic acid was papered in the same manner as in Example 1. The prepared crude sorbic acid (65 g) and a sodium hydroxide aqueous solution were mixed and gradually heated while stirring and adjusting pH of the resulting mixture to 6.0. As a result, a homogenous solution was obtained at a temperature of 75° C. The treatment with activated carbon, acidification, and crystallization procedures were then performed in the same manner as in Example 1 to yield sorbic acid. In 8.8 ml of a 1 N-NaOH aqueous solution, 1 g of the above-prepared sorbic acid was dissolved, and the light transmittance of the solution at a wavelength of 400 nm was determined with a spectrophotometer. The solution was found to have a light transmittance of 75.5%.

EXAMPLE 3

A crude sorbic acid was papered in the same manner as in Example 1. The prepared crude sorbic acid (65 g) and a sodium hydroxide aqueous solution were mixed and gradually heated while stirring and adjusting pH of the resulting mixture to 7.0. As a result, a homogenous solution was obtained at a temperature of 35° C. The treatment with activated carbon, acidification, and crystallization procedures were then performed in the same manner as in Example 1 to yield sorbic acid. In 8.8 ml of a 1 N-NaOH aqueous solution, 1 g of the above-prepared sorbic acid was dissolved, and the light transmittance of the solution at a wavelength of 400 nm was determined with a spectrophotometer. The solution was found to have a light transmittance of 75.6%.

EXAMPLE 4

Sorbic acid was prepared in the same manner as in Example 1, except that a zinc chloride-activated carbon [trade name: ZN-D, material: wood flour, total pore volume: 1.3 ml/g, F9 specific surface area: 1400 $m^2$/g, a product of Hokuetsu Carbon Industry Co., Ltd.] was used as the activated carbon. In 8.8 ml of a 1 N-NaOH aqueous solution, 1 g of the above-prepared sorbic acid was dissolved, and the light transmittance of the solution at a wavelength of 400 nm was determined with a spectrophotometer. The solution was found to have a light transmittance of 72.2%.

COMPARATIVE EXAMPLE 1

Sorbic acid was prepared in the same manner as in Example 1, except that a steam-activated carbon [trade name: NISSO-MERSAN EEP-02, material: coconut shell, total pore volume: 0.3 ml/g, specific surface area: 500 $m^2$/g, a product of Nippon Soda Co., Ltd.] was used as the activated carbon. In 8.8 ml of a 1 N-NaOH aqueous solution, 1 g of the above-prepared sorbic acid was dissolved, and the light transmittance of the solution at a wavelength of 400 nm was determined with a spectrophotometer. The solution was found to have a light transmittance of 55.4%.

What is claimed is:

1. A process for improving the light transmittance of a solution of sorbic acid or its salt produced through the decomposition of a polyester obtained from ketene and aldehyde, said process comprising the step of treating a solution containing sorbic acid or its salt so produced with a chemically activated carbon at pH ranging from 6.2 to 6.8 at temperatures ranging from 40° C. to 70° C.

2. The process of claim 1, wherein the specific surface area of the chemically activated carbon is about 1000 to 2000 $m^2$/g, and its total pore volume is about 0.8 to 1.6 ml/g.

3. The process of claim 1, wherein the chemically activated carbon is acid activated carbon.

4. The process of claim 1, wherein the chemically activated carbon is activated by zinc chloride or phosphoric acid.

5. The process of claim 1, wherein the chemically activated carbon is activated by zinc chloride.

* * * * *